United States Patent [19]

Tobey

[11] Patent Number: 5,030,097
[45] Date of Patent: Jul. 9, 1991

[54] METHOD USING A COLLOIDAL SUSPENSION OF THE RARE EARTH OXIDE AS A WETTING AGENT AND A SUSPENDING AGENT FOR MAKING DENTAL PORCELAINS

[76] Inventor: Richard G. Tobey, 211 S. Liberty St., Asheville, N.C. 28801

[21] Appl. No.: 574,534

[22] Filed: Aug. 28, 1990

Related U.S. Application Data

[60] Continuation of Ser. No. 327,421, Mar. 20, 1989, abandoned, which is a division of Ser. No. 194,159, May 16, 1988, abandoned.

[51] Int. Cl.$^5$ .................... A61C 13/00; A61C 13/083; C03C 8/16
[52] U.S. Cl. .................... 433/199.1; 106/35; 264/19; 433/202.1; 433/206; 501/17; 501/32
[58] Field of Search ............... 106/35, 312, 400, 313; 433/202.1, 206, 199.1; 264/19, 20; 501/17, 32

[56] References Cited

U.S. PATENT DOCUMENTS

| | | | |
|---|---|---|---|
| 2,332,423 | 10/1943 | Zwermann | 501/17 |
| 3,868,334 | 2/1975 | Van Loan | 501/17 |
| 3,880,662 | 4/1975 | Daskalon et al. | 106/35 |
| 4,010,048 | 3/1977 | Tesk et al. | 148/24 |
| 4,170,823 | 10/1979 | Smyth et al. | 250/461.1 |
| 4,198,244 | 4/1980 | Binns et al. | 106/35 |
| 4,264,640 | 4/1981 | Infante | 264/20 |
| 4,358,271 | 11/1982 | Sperner | 433/206 |
| 4,431,451 | 2/1984 | Mabie et al. | 501/21 |
| 4,468,251 | 8/1984 | Hausselt et al. | 106/35 |
| 4,545,923 | 10/1985 | Gradeff et al. | 252/309 |
| 4,626,514 | 12/1986 | Watanabe et al. | 106/35 |
| 4,647,401 | 3/1987 | Gradeff et al. | 106/267 |
| 4,747,876 | 5/1988 | Hakamatsuka et al. | 106/35 |
| 4,798,536 | 1/1989 | Katz | 433/212.1 |
| 4,806,507 | 2/1989 | Olby | 501/17 |

FOREIGN PATENT DOCUMENTS 0119062 9/1984 European Pat. Off. .

*Primary Examiner*—Paul Lieberman
*Assistant Examiner*—John Boyd
*Attorney, Agent, or Firm*—David M. Carter

[57] ABSTRACT

There is provided a mixture which preferably is a colloidal suspension of finely divided particles of a rare-earth oxide such as cerium oxide in a liquid. The liquid may be all water but also may include other materials such as acetic acid, 1,3-butanediol, methanol. The mixture is used as a wetting and suspending agent for opaque and build-up dental porcelains to primarily overcome the problem of discoloration of the porcelains when used with metal substrates made of dental alloys containing silver, and also to make the porcelains easier to handle and to work with.

14 Claims, No Drawings

METHOD USING A COLLOIDAL SUSPENSION OF THE RARE EARTH OXIDE AS A WETTING AGENT AND A SUSPENDING AGENT FOR MAKING DENTAL PORCELAINS

This is a continuation of copending application Ser. No. 327,421, filed Mar. 20, 1989, which is a division of Ser. No. 194,159, filed May 16, 1988, both now abandoned.

BACKGROUND OF THE INVENTION

This invention relates to the manufacture of artificial teeth. More particularly, it relates to the use of dental porcelains which are used on substrates made of silver-containing alloys where discoloration of the porcelain is a problem.

In the manufacture of dental porcelain restorations, metal substrates are fabricated and utilized as frameworks onto which porcelain is applied and fused. The porcelain forms the tooth or teeth and is intended to be functional and also aesthetic, i.e. to blend with adjacent dentition with respect to shape, contour, shade or color, translucency, etc.

When the technology of fusing porcelain to metal for the purpose of fabricating dental restorations was first developed in the 1950's, the only available appropriate dental alloys contained large amounts of gold. As gold became cost prohibitive, alloys were developed replacing the gold content with palladium and silver. These alloys are more economical and mechanically superior, however the silver contained in the alloy causes the porcelain to become discolored during and after the fusing process.

Opaque, body or dentin, and incisal porcelains are provided to the dental technician or ceramist in powdered form. The opaque powder is mixed with a wetting agent, most commonly distilled water, to a creamy paintlike consistency. It is then applied to an alloy substrate and fired in an oven for the purpose of fusing the ceramic material to the alloy. The body and incisal porcelain powders are each mixed with a wetting agent, most commonly distilled water, to a claylike moldable consistency and then applied to the opaqued metal framework and shaped in the form of a tooth or teeth. The porcelain "build-up" is then fused to the opaqued metal framework by firing it in an oven to the appropriate temperatures for the appropriate amount of time. If the metal framework contains silver, the porcelain will develop a yellow-green discoloration as this is the manifestation of the corrosive effect that the silver has on the porcelain.

In order to effectively eliminate this problem of discoloration, the technician must compromise and limit his/her choice of materials by either using an alloy substrate which is silver-free or choosing from a very limited selection of porcelains that are manufactured in such a way as to inhibit discoloration from silver but which may not be totally effective, esthetically acceptable, technically adequate, or economically feasible. Non-precious alloys are silver-free but are difficult to work with as they are hard to grind and shape, and also they are not universally accepted as being biocompatible with human tissue, as these alloys generally contain nickel, cobalt, chrome, and beryllium. Precious alloys which are silver-free contain greater amounts of palladium than alloys which do contain silver, thus becoming much more expensive. These high palladium, silver-free alloys have a tendency to deform during firing, develop a very dark oxide which is difficult to cover with opaque porcelain, and are difficult to solder because of their relatively low melting temperature. From a technical, economical, and biocompatibility standpoint, dental alloys which contain silver are superior to those which do not.

OBJECTS OF THE INVENTION

It is therefore one object of this invention to provide a material which may be used in the dental laboratory to effectively eliminate the problem of discoloration that occurs when dental porcelain is fused to alloys which contain silver in the manufacture of artificial teeth.

It is another object to provide a material for wetting and suspending dental porcelains which does not force the technician to limit his/her choice of materials, compromise his/her technique, or incur excessive expense.

It is another object to provide a material which when mixed with dental porcelain powders, the resulting mixture becomes easier to control than if mixed with water, thereby facilitating the process of fabricating porcelain fused to metal restorations.

It is another object to provide a suspending/wetting agent for porcelain which may be used in the place of distilled water, thereby allowing the technician to use the same techniques to fabricate a porcelain fused to metal restoration as would be employed with water, without adding any extra steps, extra time, or specific precautions that may lengthen or complicate the process.

It is another object to provide a porcelain suspending/wetting material which may be used with any dental porcelain or any type of dental alloy.

It is still another object to provide a simple, inexpensive method for overcoming porcelain discoloration problems in the manufacture of artificial teeth and which enables ease of handling of the porcelain.

SUMMARY OF THE INVENTION

In accordance with one form of this invention, there is provided a mixture containing solid and liquid materials which are to be mixed with powdered porcelain which is to be applied over portions of a metal substrate in the formation of artificial teeth. The metal substrate may contain silver. The solid parts of the mixture includes an amount of a rare-earth oxide which is preferably suspended in the liquid which is primarily water. The liquid may also include an amount of acetic acid, a Di-Hydric alcohol such as 1,3-butanediol and a simple alcohol such as methanol.

It has been found that the above described mixture, when used with powdered opaque dental porcelain and powdered build-up dental porcelain, aids in the handling characteristics of the resulting porcelain paste enabling the ceramist to more easily perform the work required in forming the teeth. Furthermore, if the mixture is used with a metal substrate containing silver, discoloration of the teeth during and after the firing of the porcelain is substantially prevented.

DESCRIPTION OF THE PREFERRED EMBODIMENTS

The preferred formulation is set forth below:
0.25% wt. Cerium Oxide [$CeO_2$]
0.0312–0.0375% wt. Acetic Acid [$CH_3COOH$]
1.0% wt. 1,3-Butanediol [$CH_2OHCH_2CHOHCH_3$]
0.75% wt. Methanol [$CH_3OH$]

Balance Distilled Water [H2O]

Preferably the mixture of the subject invention includes an amount of colloidal cerium oxide (20% wt. cerium oxide, 2.5-3% wt. acetic acid and the remainder water), forming 1.25% wt. of the mixture. Colloidal cerium oxide is commercially available from Rhone-Poulenc, Inc. under the tradename Colloidal Cerium 20%. The cerium oxide, which is one rare-earth oxide which may be used, is suspended as small particles in the mixture. 1.0% wt. of 1,3-butanediol and 0.75% wt. methanol is added to the colloidal cerium oxide with the balance of the mixture being distilled water.

The mixture is used as a wetting and suspending agent for dental porcelains. The above-described colloid is mixed separately with a typical opaque dental porcelain and a typical build-up dental porcelain into a workable consistency. The treated opaque porcelain is painted onto a metal alloy substrate which may contain silver. The opaque porcelain is fired in an oven and becomes fused to the metal substrate. A tooth is then formed over the opaque porcelain with the treated build-up porcelain and it is also fired in an oven and becomes fused to the metal substrate. The treated porcelains are easy to handle and shape and the fired porcelain does not discolor even though a silver alloy substrate may be used.

It is believed that the following ranges of the materials referred to above will also provide adequate results: 0.1% to .4% wt. colloidal cerium oxide 20%, 0.5% to 5% wt. 1,3-butanediol, 0.5% to 6% wt. methanol, with the balance distilled water. Expressed another way, the ranges are 0.02% to 0.8% wt. cerium oxide, 0.0025% to 0.12% wt. acetic acid, 0.5% to 5% wt. 1,3-butanediol, 0.5% to 6% wt. methanol, with the balance distilled water. Variations of the formula were used to establish the limits of each component. Too much cerium caused cloudiness, too much 1,3-butanediol caused cracking of the porcelain and cloudiness, too much alcohol caused too rapid drying, not enough of the individual components diminished effectiveness.

It is believed that the 1,3-butanediol helps lengthen the drying time and thus gives the ceramist more working time with the material. Furthermore, it is believed that the 1,3-butanediol aids in the consistency of the material, and thus is a handling aid. It also helps keep the mixture homogeneous.

It is believed that the methanol helps the material to evaporate more evenly, and also helps with handling the material and with the dispersion of solid particles within the porcelain thus preventing aglomeration of the porcelain particles. Furthermore, the methanol acts as a thinner, thereby making it easier to draw the moisture out during building and condensing.

The cerium oxide is the ingredient which prevents the corrosion effect that the oxidation and ionization of the silver portion of the alloy has on the porcelain material during firing. Furthermore, it is believed that the colloidal cerium oxide also aids in the dispersion and suspension of the porcelain particles and thus helps somewhat in its handling. The distilled water, of course, lowers the concentration of the other parts of the mixture.

The preferred colloidal suspension of cerium oxide is 20% wt. of cerium oxide, 2.5 to 3% by weight of acetic acid with the balance of the suspension being water. The acetic acid helps to maintain the cerium oxide in suspension.

EXAMPLE 1

As a suspending agent for dental porcelains, the following formulation of the mixture has been tested and compared with using distilled water alone: 1.0% wt. 1,3-butanediol, 0.75% wt. methanol, 1.25% wt. colloidal cerium oxide 20%, available from Rhone-Poulenc, Inc. under the tradename Colloidal Cerium 20%, with the balance distilled water.

The above described mixture was used with powdered Crystar porcelains distributed by Unitec Corporation of Monrovia, Calif. The porcelains were opaque shade A1 and body shade A1 and incisal shade 58.

Two individual copings or metal substrates were fabricated of Jeneric Rx 91 alloy which contains 53.5% Pd (palladium) and 37.5% Ag (silver).

In Sample 1, the novel mixture was first mixed with the opaque porcelain powder until a creamy, paintlike consistency was established, and applied to one of the metal copings.

In Sample 2, distilled H2O was mixed with the opaque porcelain powder to a workable consistency, and applied to the other metal coping. These two copings were then fired in a porcelain furnace from 1200° F. to 1800° F. at 100° F. per minute under 28 inches of vacuum. The vacuum was released at 1750° F., and when the temperature reached 1800° F., the copings were removed and allowed to cool. This entire opaquing process was then repeated, as is typical in the dental laboratory.

After the second opaque bake, the copings were allowed to cool to ambient temperature. For Sample 1, the body and incisal porcelain powders were then separately mixed with the novel mixture until a workable consistency was established. This mixture was then applied to the Sample 1 coping and built and formed into the shape of a tooth. For Sample 2, the body and incisal porcelain powders were mixed with distilled H2O until a workable consistency was established, and then this mixture was applied to the Sample 2 coping and shaped to form a tooth. These two porcelain "build-ups" were allowed to dry appropriately and then fired in a porcelain oven from 1200° F. to 1700° F. at 100° F. per minute under 28 inches of vacuum. The vacuum was released at 1650° F. and the porcelain crowns were removed when the temperature reached 1700° F. After cooling it was observed that the porcelain crown that was built and shaped using distilled water as the wetting agent or medium (Sample 2) displayed a significant yellow-green discoloration. The crown that was built and shaped using the novel mixture as a wetting agent or medium (Sample 1) displayed no such discoloration and the shade of the crown was consistent with the Vita-Lumin Shade Guide (Shade A-1).

These two porcelain crowns were then ground lightly to enhance their shape and anatomy, and then fired in the furnace again according to the same parameters as the first bake. After cooling it was observed that the discoloration of Sample 2 became even more significant whereas Sample 1 displayed no such discoloration.

The two crowns were once again ground lightly and then treated to a glaze bake, i.e. fired in the furnace from 1200° F. to 1700° F. at 100° F. per minute in air (no vacuum) and held at 1700° F. for 30 seconds. They were then removed and after becoming cool, the Sample 2 crown displayed significant discoloration while the Sample 1 crown displayed no discoloration.

This establishes that under normal dental laboratory procedures the invention effectively eliminates the problem of discoloration, and also that the invention improves the handling of the materials.

EXAMPLE 2

Two additional copings were then fabricated of the same Pd-Ag alloy and the entire process of Example 1 was repeated, with the exception that each crown was given two opaque bakes, four buildup bakes under vacuum, and two glaze bakes in air. Sample 3, which was fabricated using distilled water, displayed significant yellow-green discoloration. Sample 4, which was fabricated using the mixture invention displayed no discoloration. This experiment establishes that even under severe conditions, the invention effectively eliminates the discoloration caused by the silver in the alloy.

EXAMPLE 3

Two translucent shade tabs of porcelain were fabricated, one mixed and fired with distilled water only and one mixed and fired with the novel mixture described in Example 1, through one vacuum bake, one air natural glaze, and were fired on platinum foil containing no silver. Neither the water nor the mixture had any effect on the shade or translucency. The porcelain which was suspended with the novel mixture however was easier to handle. This experiment establishes that the novel mixture has no negative effect on the porcelain, i.e. that the shade and translucency does not become altered.

The above experiments were repeated using several different brands of porcelains, with similar results.

EXAMPLE 4

Example 1 was repeated except that in formulating Sample 1, the novel mixture was added to the body and incisal porcelain and distilled water only was added to the opaque. Discoloration did not occur after firings.

In addition to the specific formulation used in the examples set forth above, it is believed that other related materials may be utilized in the formulation. For example, it is believed that other rare-earth oxides may be used in place of the cerium oxide, such as, for example, lanthanum, praseodynium, neodymium, promethium, samarium, and europium oxides. Furthermore, other low molecular weight alcohols such as ethanol, may be used in place of methanols so long as their molecular weights or carbon chain are not so high as to cause carbonizing or blackening of the material during firing. Furthermore, it is believed that Di-Hydric alcohols such as, for example, propelene-glycol or glycyl alcohols such as glycerin can be used in place of the 1,3-butanediol. It has been observed that by using 1.25% colloidal cerium oxide 20% in water alone the discoloration did not occur which would normally occur with a porcelain mounted on a silver alloy substrate.

As to the handling characteristics utilizing the novel mixture, the opaque porcelain mix becomes creamy and smooth allowing it to be easily applied to the metal substrate. The novel mixture causes the body and incisal porcelain mixtures to become easier to handle and easier to apply and to condense with less slumping, easier to carve anatomy and easier to shape. The novel liquid also reduces cracking and tearing of porcelain during firing, facilitating the fabrication process.

In some cases when water alone is used as the wetting/suspending agent, discoloration has been observed where solders which contain silver have been used on a metal substrate which does not itself contain silver. It has been observed that the use of the novel mixture will also prevent discoloration in those situations.

From the foregoing description of the preferred embodiments of this invention, it will be apparent that many modifications may be made therein without departing from the true spirit and scope of the invention.

I claim:

1. A method of fabricating an artificial tooth fused to a metal substrate comprising the steps of:
    mixing a concentrated colloidal suspension of a rare-earth oxide with water thereby forming a diluted colloidal suspension of said rare-earth oxide; said rare-earth oxide in said diluted colloidal suspension being in the range of from 0.02% to 0.8% weight of said diluted colloidal suspension;
    combining said diluted colloidal rare-earth oxide suspension with porcelain into a workable consistency;
    applying a portion of the porcelain/rare-earth oxide mixture to a metal substrate;
    forming a tooth on the substrate with the porcelain/rare-earth oxide mixture;
    fusing the porcelain/rare-earth oxide mixture to the metal substrate with heat; said tooth not being substantially discolored during said fusing.

2. A method as set forth in claim 1 wherein said diluted rare-earth oxide suspension includes 0.5% to 5% weight 1,3-butanediol, 0.5% to 6% by weight methanol and water; said rare-earth oxide being cerium oxide.

3. A method as set forth in claim 2 wherein said substrate is made from silver alloy.

4. A method for the prevention of discoloration of an artificial tooth made primarily from porcelain comprising the steps of:
    mixing a colloidal suspension containing a rare-earth oxide and water with dental porcelain powder; said rare-earth oxide taken from the group consisting of an oxide of cerium or an oxide of lanthium; said rare-earth oxide being in the range of from 0.02% to 0.8% weight of said suspension;
    applying said mixture to a metal substrate which supports the artificial tooth;
    forming said artificial tooth with said mixture;
    fusing said tooth to said substrate with heat; said tooth not being substantially discolored during said fusing.

5. A method as set forth in claim 4 wherein said colloidal suspension also includes acedic acid.

6. A method as set forth in claim 5 wherein said colloidal suspension is formed by adding a concentrated colloidal suspension to said water; said concentrated colloidal suspension having 20% weight cerium oxide, and from 2.5% to 3% weight acedic acid all of which being in water.

7. A method as set forth in claim 4 wherein said substrate contains a silver alloy.

8. A method as set forth in claim 4 further including the steps of adding an amount of 1,3-butanediol, and an amount of methanol to said colloidal suspension resulting in 1,3-butanediol in the range of 0.5% to 5% weight and methanol in the range of 0.5% to 6% weight.

9. A method as set forth in claim 4 further including the steps of adding 1,3-butanediol to said colloidal suspension resulting in a range of 0.5% to 5% by weight, and adding methanol to said colloidal suspension resulting in a range of 0.5% to 6% by weight; said rare earth oxide being cerium oxide in the range of 0.027% to 0.8% weight of said colloidal suspension; said suspension including acetic acid in the range of 0.0025% to 0.12% by weight and the balance being distilled water.

10. A method as set forth in claim 9 wherein said 1,3-butanediol is 1.0% weight, said methanol is 0.75% weight, and said cerium oxide is 0.25% weight.

11. A method as set forth in claim 9 wherein said acetic acid is 0.012% to 0.0375% weight.

12. A method as set forth in claim 4 wherein said colloidal suspension includes 0.1% to 0.4% weight cerium oxide and the balance water.

13. A mixture as set forth in claim 12 wherein said cerium oxide is 0.25% weight of said colloidal suspension.

14. A method as set forth in claim 4 wherein said metal substrate includes a silver paladium alloy.

* * * * *